United States Patent [19]

Gordon et al.

[11] Patent Number: 4,842,610
[45] Date of Patent: Jun. 27, 1989

[54] DEPILATORY COMPOSITIONS AND METHODS

[75] Inventors: Harry W. Gordon, Wantagh; Kenneth Chung, Greenlawn, both of N.Y.

[73] Assignee: Del Laboratories, Inc., Farmingdale, N.Y.

[21] Appl. No.: 121,953

[22] Filed: Nov. 28, 1987

Related U.S. Application Data

[63] Continuation of Ser. No. 863,930, May 15, 1986, abandoned, which is a continuation of Ser. No. 672,461, Nov. 19, 1984, abandoned, which is a continuation-in-part of Ser. No. 475,460, Mar. 15, 1983, abandoned.

[51] Int. Cl.$^4$ ................................. C14C 1/00
[52] U.S. Cl. .......................... 8/160; 8/161; 106/162
[58] Field of Search ...................... 8/160, 161; 106/162

[56] References Cited

U.S. PATENT DOCUMENTS

| | | | |
|---|---|---|---|
| 1,285,247 | 11/1918 | LaForge | 106/162 |
| 2,417,882 | 3/1947 | Neary | 8/160 |
| 3,426,137 | 2/1969 | Philpitt et al. | 8/161 |
| 3,563,694 | 2/1972 | Minton | 8/160 |
| 3,850,838 | 11/1974 | Guckenberger et al. | 514/779 |

FOREIGN PATENT DOCUMENTS

| | | | |
|---|---|---|---|
| 2918422 | 1/1980 | Fed. Rep. of Germany | 8/160 |
| 0604711 | 9/1978 | Switzerland | 8/160 |
| 0901624 | 1/1961 | United Kingdom | 8/160 |
| 1242083 | 8/1971 | United Kingdom | 8/160 |

OTHER PUBLICATIONS

*Soap, Perfumery & Cosmetics,* pp. 169-170 (Mar., 1940).
*The Merck Index,* 9th ed., Abst. #210 (1976).
Ruemele, *Amer. Perfumer & Aromatics,* p. 53 (Jul. 1960).
Chem. Abstract 105:228845b (1986).
Chem. Abstract 98:90791j (1983).

*Primary Examiner*—Dale R. Ore
*Attorney, Agent, or Firm*—Kirschstein, Ottinger, Israel & Schiffmiller

[57] ABSTRACT

Hair removal compositions useful for cosmetic, medical and other purposes comprise 90 to 99.5% corn syrup and 0.5% to 10% added water by weight. The compositions can also include additives such as germicides, preservatives and opacifiers. The compositions are used by applying them to the surface of the skin in a hairy area, pressing a sheet of paper or other fibrous material against the area and subsequently lifting the sheet of fibrous material or peeling it off the skin surface. The compositions are also useful in removing blemishes and scaly, flaky or dry skin.

1 Claim, No Drawings

DEPILATORY COMPOSITIONS AND METHODS

This application is a continuation of application Ser. No. 863,930 filed May 15, 1986, now abandoned, which, in turn, is a continuation of abandoned application Ser. No. 672,461 filed Nov. 19, 1984, which, in turn, is a continuation-in-part of abandoned application Ser. No. 475,460 filed Mar. 15, 1983.

BACKGROUND OF THE INVENTION

1. Field of the Invention:

The present invention relates to a composition useful in the removal of human body hair and methods for utilizing the same.

2. Description of the Prior Art:

Since time immemorial, people have sought to remove unwanted hair from the body for cosmetic, medical, social and other reasons. The most primitive and probably the earliest methods devised for removing such unwanted hair were mechanical in nature, e.g., grasping a single hair or a group of hairs by their ends and forcibly plucking them out of the skin by their roots, or effecting the same operation by use of tweezers or other mechanical grasping devices. Shaving and abrasion of the skin by use of a razor or a knife or any abrasive has also been practiced for millenia as a method for hair removal.

Many centuries ago it was discovered that certain naturally occurring chemical substances, such as certain plant extracts, had the ability to cause the removal of human body hair when applied to a particular skin surface. Many of these naturally occurring chemical depilatories, however were quite harsh, causing substantial irritation to human skin, particularly to sensitive skin areas such as the face, and were frequently malodorous as well.

In modern times, several new depilatory agents and methods have been developed. Electrolysis, whereby a fine wire is inserted into each individual hair follicle and a mild electric current is sent through the wire to destroy the hair-forming cell at the base of the follicle, is a widely-utilized technique for cosmetic hair removal. In addition, X-ray techniques have been used whereby a brief exposure of a skin area to a relatively mild dosage of radiation caused the hair in that area to fall out.

Probably the most widely used depilatory agents developed in modern times are commercially-sold creams and ointments which contain as their active ingredient disulfide bond breakers such as salts of mercaptan acids, particularly salts of thioglycolic acid. These salts attack the most recently formed portion of the hair shaft, that is, the part closest to the skin surface. They act by rupturing the disulfide bonds in the keratin protein found in the hair shaft, weakening the hair and causing it to be ruptured at the surface of the skin, an effect somewhat similar to closely shaving the skin area. The hair root, however, remains in the follicle and the disulfide bond breaking salts have a deleterious effect on the skin and give rise to unpleasant odors.

Another cosmetic hair removal technique currently practiced in the art, primarily by cosmeticians and other professionals, involves the application of flowable wax to a hairy area. The wax is allowed to cool and harden, whereupon it enmeshes the hair which it contacts. The hardened wax then is stripped from the skin, pulling out the enmeshed hair by its roots. New hairs generally will not appear at the skin surface for a period of weeks.

In the medical sphere, hair removal is frequently an important part of pre-surgical preparation. To the present day, the almost universally practiced method for removing the hair from the area where an operation is to be performed is to shave the area with a razor and a suitable lubricated or cream. Because even the closest shave leaves a small amount of stubble, and because hair growth reappears fairly quickly after shaving, the shaving procedure is normally performed almost immediately before the patient is brought into the operating room. Although more efficient and long-lasting hair removal methods are available, such as the use of chemical depilatories or flowable waxes described above, such techniques are disfavored for pre-surgical use because of their tendency to cause irritation of the skin area which can lead to possible infection and other unwanted complications.

It readily can be seen that each of the hair removal methods currently practiced in the art suffers serious drawbacks. Plucking manually or with tweezers is extremely time-consuming, painstaking work and is rather painful and irritating. Shaving is a more rapid hair-removal method, but it tends to cause nicks and cuts in the skin and, at best, removes hair only down to the skin surface. Moreover, frequent shaving often stimulates rapid hair growth.

Chemical depilatories such as the thioglycolate salts are somewhat toxic and also irritating, particularly to sensitive skin areas or to individuals with particularly sensitive skin. Moreover, these depilatories must be left on the skin for a minimum of ten and frequently fifteen minutes for effective hair removal, increasing the time for the overall procedure and the risk of skin irritation.

Hot wax methods are relatively complex and necessitate the use of heating equipment, equipment for applying the molten wax to the skin, and wax removal means. Moreover, the molten wax is frequently at a temperature of 75° C. and even higher, causing at least a burning sensation to most subjects and in some cases even entailing a risk of actual burn damage to the skin.

More recently, attempts have been made to develop, hair-removal compositions and methods which will overcome the aforementioned drawbacks of the prior art; i.e. which are non-irritating, can be used without heating, and yet cleanly and thoroughly remove hair without allowing rapid return growth. For example, attempts have been made to formulate sticky semi-liquid compositions from unrefined sugar, said compositions to be used by applying them to the hairy area and then pressing paper or similar material against the area and pulling away the hair enmeshed by the sticky composition. Such compositions have not been commercially feasible, however, because unrefined sugar is expensive and not widely available for commercial use in this country. Moreover, there is some technical difficulty in making suitable homogeneous formulations of unrefined sugar on a commercial scale. In addition, compositions made with unrefined sugar are naturally dark brown in color and very unappealing for use in commercial cosmetic products. Nor do such compositions have stable shelf lives long enough to be commercially practical.

Electrolysis methods are expensive, somewhat painful and must be performed by a professional utilizing specialized expensive equipment. X-ray techniques are unsatisfactory because they entail a far greater risk of permanent damage than is normally justified for cosmetic hair removal.

Thus, to the present date, no commercially feasible hair-removal compositions have been developed which are safe, non-toxic, non-irritating, have a long lasting effect, require no heating or mechanical devices for their use, and are acceptable for medical and pre-surgical procedures.

SUMMARY OF THE INVENTION

1. Objects of the Invention:

It is an object of the present invention to provide compositions for use in the removal of human hair that are safe, effective, non-irritating and non-toxic and that can be utilized in simple and inexpensive hair-removal methods.

An additional object of the present invention is to provide compositions as described above which can be applied at room temperature.

A further object of the present invention is to provide compositions as described above which can be formulated on a commercial scale with readily available and relatively inexpensive ingredients.

Still another object of the invention is to provide compositions as described above which comprise corn syrup as their principal ingredient.

Still a further object of the present invention is to provide compositions as described above which include, in addition to corn syrup, additives such as germicidal, preservative and/or opacifying agents.

Yet another object of the present invention is to provide hair-removal methods which are rapid, inexpensive and useful in medical and pre-surgical procedures.

Yet a further object of the present invention is to provide methods as described above utilizing the novel corn syrup containing composition of the present invention.

Still another object of the present invention is to provide methods of blemish and scale removal utilizing the novel composition of the present invention.

2. Brief Description of the Invention:

In keeping with these objects and others which will become apparent hereinafter, the present invention resides, briefly stated, in hair-removing compositions which essentially comprise about 90–99.55 corn syrup and about 0.5–10% water by weight. The term "corn syrup" used throughout this specification and its appended claims denotes the corn syrup known as "regular" corn syrup which is a corn syrup having a D.E.* of from about 40 to about 44. A typical regular corn syrup useful in the invention has a D.E. of 42, a monosaccharide content of about 19%, a disaccharide content of about 14%, a trisaccharide content of about 11.5%, a tetrasaccharide content of about 10%, a pentasaccharide content of about 8.5%, a hexasaccharide content of about 6.5%, a heptasaccharide content of about 5.5%, and a higher saccharide content of about 25%. Corn syrup, of course, consists of a mixture of naturally occurring sugars derived from corn, and usually includes such sugars as dextrose, maltose, maltotriose and higher saccharides. Corn syrup is very widely available in the United States and is produced by major food processors at the level of millions of pounds a year. It is known and purchased by the name "corn syrup" throughout the world.

*D.E. is the dextrose equivalent of a starch hydrolyzate, i.e. the total amount of ordinary sugars, expressed as an hydrous dextrose, present in a dry hydrolyzate.

Optionally, the corn syrup compositions of the present invention can include additives such as germicidal and opacifying agents, preservatives, coloring agents, and so on.

It has been discovered that the naturally sticky and adhesive nature of corn syrup, is considerably enhanced when a small amount of water is mixed therewith. Homogeneous mixtures of small amounts of water with corn syrup having particular levels of total solids contents and of higher saccharides have been discovered to be extremely useful in hair removal procedures. To effect these procedures, the corn syrup-based composition is simply applied evenly to the hairy area and a sheet of paper or other fibrous material is pressed against the area. The corn syrup composition enmeshes the hair over which it is applied and causes it to adhere to the paper so that when the paper is lifted away from the area, the hair in the area is pulled out by its roots.

The hair-removing compositions of the present invention are non-toxic and non-irritating to even the most sensitive skin areas. Moreover, they have no offensive odor and can easily be washed off with soap and water; nor does their use create an offensive odor.

The compositions of the present invention can also be used effectively in removing dried blemishes, such as blackheads, and scaly or flaky skin patches. As with the hair-removal techniques, the composition is simply applied to the affected area and then a sheet of paper or similar material is pressed against the area and lifted away.

In general, the composition of the present invention is safer, less irritating, less odorous and more useful in pre-surgical and medical procedures then any prior art chemical depilatories or waxes. Because of the long-lasting effect of their removal performed with this composition, pre-surgical hair removal need not be performed immediately prior to surgery, as with currently used shaving techniques, but can be performed even 24 hours or longer prior to surgery and yet leave a more hair-free surface for a surgical incision than is the case with shaving procedures.

DETAILED DESCRIPTION OF THE INVENTION

The hair-removing composition of the present invention differs markedly from prior art chemical depilatories or waxes in that it is composed of inexpensive, readily available, safe (in fact, even food-grade), non-irritating materials and can be utilized at room temperature. This is in marked contrast to the toxic, irritating, highly alkaline thioglycolate salts used in most commercially available chemical depilatories and in contrast to the common beeswax-rosin depilatory waxes which must be heated to molten form before being applied to the skin surface to be treated.

Whereas certain dry waxes have been used in the prior art to remove hair at cold or room temperatures, such as in the form of wax-coated paper strips, the irritation caused by these wax strips is considerable and greatly exceeds that caused by use of the liquid compositions of the present invention.

More specifically, the compositions of the present invention comprise about 90–99.5% corn syrup and 0.5–10% added water by weight. The term "added water" refers to water added to and apart from the water content of corn syrup itself. It has been discovered that, for purposes of hair-removal procedures, corn syrups comprising 30–80% higher saccharides (e.g., polysaccharides such as tetrasaccharides, pentasaccharides, hexasaccharides, heptasaccharides and still higher saccharides) by weight and an overall solids content of approximately 75–95% by weight (the balance water) are most effective and show the best adhesion and viscosity properties when mixed with small added amounts of water. Furthermore, it has been found that the optimum amount of water to be added to the composition can be increased as the higher saccharide content of the corn syrup is increased, up to a maximum of about 10% water by weight.

Usable corn syrups have a D.E. range of about 30 to about 70 and are typified as to constitution in the following Table:

| D.E. | % saccharides by weight | | | | | | | |
|---|---|---|---|---|---|---|---|---|
| | Mono - | Di - | Tri - | Tetra - | Penta - | Hexa - | Hepta - | Still Higher |
| 30 | 10.5 | 9.5 | 8.5 | 8.0 | 7.0 | 6.0 | 5.0 | 45.5 |
| 42 | 18.5 | 14.0 | 11.5 | 10.0 | 8.5 | 6.5 | 5.5 | 26.0 |
| 54 | 20.5 | 18.0 | 13.0 | 9.5 | 7.5 | 5.5 | 4.5 | 11.5 |
| 60 | 36.0 | 19.5 | 13.0 | 8.5 | 6.5 | 4.5 | 3.0 | 9.0 |

A corn syrup of choice for use in the present invention has a higher saccharide (tetra and higher) content of about 55% and a total solids content of 83.5%. This syrup forms a highly effective hair-removing composition when about 0.5–2% water by weight is added thereto. The water used in the composition of the present invention is preferably distilled or deionized water for reasons of purity, stability and homogeneity.

In addition to the basic corn syrup and water ingredients, compositions of the present invention can comprise additives such as slight amounts of a germicide and a preservative, and an opacifier. Germall 115, constituting imidazolidinyl urea as its active ingredient, is an effective germicidal additive which greatly reduced the possibility of infection of the skin or follicles during or after the hair-removal process. Styrene/PVP (polyvinyl pyrrolidone) copolymers are useful opacifying agents. Examples of preservatives which can be utilized include the alkylparabens (alkyl p-hydroxybenzoates), among others.

Of course, in formulating commercial compositions including the novel corn syrup-based composition of the present invention, perfume, color, lubricant, propellant and other additives may be utilized as deemed necessary in accordance with conventional practices in the cosmetics and pharmaceutical industries. However, unlike prior art mercaptan-based depilatories, the composition of the present invention need not be formulated in mineral oil or other pharmaceutically acceptable ointment or cream bases in order to be safely and effectively utilized.

To remove unwanted hair from a particular body area, the corn syrup-based compositions of the invention are applied to the skin surface to form a uniform coating. Subsequently, and without the necessity for waiting any substantial period of time, a sheet of paper or similar fibrous material is firmly pressed against the area coated with the corn syrup composition and lifted or peeled away therefrom. The hairs enmeshed by the corn syrup adhere to the paper or other material and are easily lifted away from the skin and pulled out by their roots. In most cases, renewed hair growth in the area is unlikely for at least a week or more, and may not occur for several weeks.

Synthetic fibrous paper material has been found most useful for performing hair-removal procedures with compositions of the present invention because it is strong enough not to fall apart when peeled away from the skin and yet forms a strong adhesive bond with the corn syrup-based compositions.

The corn syrup-based compositions of the present invention, even without additives, have no noxious odor or aroma, in distinct contrast to many chemical depilatories of the prior art. And, unlike certain commercially unsuccessful hair-removing compositions which were formulated with unrefined sugar, which were heavy and dark brown, the novel compositions are light and pleasant in appearance and are easily formulated in smooth, free-flowing form. Moreover, the materials for producing the compositions for the invention are easily and cheaply available on a large scale and can be inexpensively mixed on a commercial scale with ease and little technical sophistication. The unrefined sugar which provided the base for certain prior art depilatories, on the other hand, is not readily available on a commercial scale in the United States.

Compositions of the present invention can be produced by simply mixing the corn syrup, water and other chemically compatible additive ingredients in a vessel and heating the same mildly to about 50°–75° C., with moderate stirring.

As will be appreciated by those skilled in the art, hair-removal procedures and techniques which are enabled by use of the safe, inexpensive, non-irritating compositions of the present invention are more rapid and otherwise superior to prior art methods.

Using the novel compositions, there is no need to wait 10 to 15 minutes or more after application as is the case with thioglycolate-based compositions; no need to utilize heating equipment to melt wax or solid compositions; no need to wait until the molten wax hardens on the skin surface before it can be removed; and certainly no need to engage in lengthy and complex instrumental procedures as are entailed by electrolysis and X-ray techniques.

Because of the many advantages of the compositions of the present invention in safely and effectively removing unwanted hair, these compositions are of particular value in medical and pre-surgical procedures. Present methods for removing the hair from an area where a surgical incision or other procedure is to be performed are undesirable in that they require great care to avoid nicking or cutting the skin, are time-consuming, must be performed almost immediately before the surgical or medical procedure, and in most instances still leave some stubble. On the other hand, by using the methods provided by the present invention, the corn syrup-based compositions can be applied quickly and smoothly to the area of interest even 24 hours or longer before the medical or surgical procedure is to be performed, and the unwanted hair can be lifted out by its roots with little or no danger of infection of the surrounding skin. Thus, it may be seen that the hair-removal method enabled by the corn syrup-based compositions of the present invention are superior to hair-removal techniques currently practiced in hospitals and medical facilities in terms of safety, time savings and convenience.

The ability to remove the hair from a body area 24 hours or more prior to the performance of a medical or surgical procedure is of substantial significance in many instances. Rather than hurriedly hsaving a patient immediately prior to moving him into the operating room, a thorough and unhurried procedure can be performed well before the operation which would permit ample time for inspection of the area and reapplication of the hair-removal compositions, if necessary.

The chemical depilatories and waxes of the prior art are undesirable for medical and surgical use not only because of their irritating tendencies, leading to possible skin damage and infection, but also, in the case of depilatories, because they do not remove the hair at the root level but merely break it off at the skin surface; and in the case of the waxes, because the procedure for melting the wax and removing it is relatively lengthy and complicated and involves bringing in specialized equipment to the treatment area which is not always readily available. These drawbacks are entirely overcome by use of the compositions of the present invention.

The corn syrup-based compositions of the inventions are also useful in safely removing dried skin blemishes, such as blackheads and scaly or flaky skin. The techniques for such blemish, scale or flake removal are identical to those practiced for hair removal. The composition is simply applied uniformly to the affected skin area to be treated and a sheet of paper or other fibrous material is pressed against the affected area and peeled or lifted away, removing the adhered dead skin or blemish. The novel compositions are especially valuable in such techniques where it is of paramount importance not to permit any alkaline, irritating or toxic substances to come in contact with the affected skin area and possibly further aggravate the condition being treated.

In general, it will be appreciated by those skilled in the cosmetic and medical arts that the novel compositions and methods of the present invention are safe, rapid, inexpensive, efficient and greatly superior to the compositions available and methods practiced in the prior art.

Following is a specific illustrative example of a hair removal composition in accordance with the present invention (which, as described above, is also useful for blemish or dried skin removal) as well as a method of using the same. This example is not intended, however, to limit or restrict the scope of the invention in any way and should not be construed as identifying specific materials, parameters or ranges which must be utilized exclusively in order to practice the present invention.

EXAMPLE

One hundred pounds of a hair-removal composition according to the present invention was prepared by mixing in a reaction vessel 98 lbs., 2.4 oz., of Clearsweet 43–44.5 corn syrup (Cargill, Inc., Cedar Rapids, Iowa), 13.6 oz. of deionized water, 8 oz. of Polectron 430, a styrene/PVP copolymer, 5.6 oz. of Germall 115 and 2.4 oz. of methylparaben. The ingredients were mixed with moderate stirring at 50°–75° C. until a thorough homogeneous mixture was achieved. Said corn syrup contained, by analysis:

Total solids content—83.5%
Moisture content—16.5%
Higher saccharides—55% (of dry solids) [approximately that of higher saccharides of D.E. 42 of previous Table]
Dextrose—19% (of dry solids)
Maltose—14% (of dry solids)
Maltotriose—12% (of dry solids)
Ash—0.3%
Nitrogen—0.008%

Said corn syrup had a density of 11.987 lbs./gallons at 100° F., a dextrose equivalent value of 43, a Baumé at 100° C. of 44.5 and a refractive index at 45° C. of 1.5012. Moreover, said corn syrup had a specific gravity at 100° F. of 1.439 and a pH of 4.7 in a 1:1 solution in water. The viscosity of said corn syrup, in centipoises, was as follows:

80° F.—700,000 cps.
100° F.—110,000 cps.
120° F.—26,000 cps.
140° F.—8,500 cps.
160° F.—3,000 cps.

After mixing, the composition had a pleasant, light-colored appearance and little odor.

Animal safety tests performed on the above-described composition showed that the composition was not a primary dermal irritant, was a minimal ocular irritant and had a very low oral toxicity level. Human patch tests showed that the composition caused no primary irritation or sensitization and showed no indication of sensitization potential.

In panel testing on human beings, the composition proved to be effective and pleasant for the great majority of participants. In fact, the composition was discovered to be less painful than certain other "cold waxing methods" currently available commercially, which entail adhesive strips or strips containing cold wax which are placed over the hairy area and then removed. It is believed that less painful results are achieved with the compositions of the present invention because the liquid composition softens the top dead layer of the skin before exfoliating it along with the hair being removed.

In the panel testing, the composition described above was applied to the test area in a thin coating and a piece of synthetic fibrous paper was pressed firmly against the area. The synthetic fibrous paper was then rapidly removed in a direction opposite the direction of hair growth. Very efficient and relatively painless results were achieved by this method.

It will thus be seen that there is provided a composition and methods which achieve the various objects of the invention and where are well adapted to meet the conditions of practical use. As various possible embodiments might be made of the above invention and as various changes might be made in the embodiments above set forth, it is to be understood that all matter herein described is to be interpreted as illustrative and not in a limiting sense.

What is claimed as new and desired to be protected by Letters Patent is set forth in the appended claims.

We claim:

1. A method of removing body hair, comprising the steps of:
   (A) applying as a coating to a hairy area a depilatory composition consisting of
      (i) about 90% to 99.5% by weight of the composition consisting of a corn syrup mixture composed of a plurality of different saccharides having a viscosity of about 700,000 cps at about 80° F. and a dextrose equivalent in a range from about 40 to 44, said corn syrup mixture having an overall solids content in the range from about 75% to 95% by weight, and a water balance content in a range from about 25% to 5% by weight,
      (ii) about 10%–0.5% by weight of the composition consisting of added distilled/deionized water,
      (iii) a germicidally effective amount of imidazolidinyl urea, (iv) an effective preservative amount of an alkyl p-hydroxybenzoate, and
(v) an effective opacifying amount of styrene polyvinyl pyrrolidone;
(B) pressing a fibrous material sheet against the composition-coated hairy area to enmesh hair in the coating; and
(C) lifting the sheet away from the hairy area with the hair from the hairy area embedded in the coating.

* * * * *